United States Patent [19]
Shinozuka

[11] Patent Number: 4,865,017
[45] Date of Patent: Sep. 12, 1989

[54] ENDOSCOPIC OPERATION INSTRUMENT
[75] Inventor: Minoru Shinozuka, Tokyo, Japan
[73] Assignee: Olympus Optical Co., Ltd., Tokyo, Japan
[21] Appl. No.: 210,755
[22] Filed: Jun. 23, 1988
[30] Foreign Application Priority Data
  Jul. 10, 1987 [JP] Japan .............................. 62-105258[U]
[51] Int. Cl.$^4$ .......................... A61B 1/00; A61B 17/22
[52] U.S. Cl. ......................................... 128/4; 128/328
[58] Field of Search ................ 128/4, 5, 6, 7, 328
[56] References Cited
U.S. PATENT DOCUMENTS
  4,592,341  6/1986  Omagari et al. ..................... 128/4
  4,682,599  7/1987  Konomura ........................... 128/328

Primary Examiner—William H. Grieb
Attorney, Agent, or Firm—Kenyon & Kenyon

[57] ABSTRACT

An endoscopic operation instrument according to the present invention comprises an operating portion formed by a plurality of elastic wires or a folded-back elastic wire received in the distal end of a flexible sheath, the elastic wires or the folded-back elastic wire being bent in the intermediate portion, wherein the bent portions of the elastic wires are located at different positions. Thus, the handling of the instrument is facilitated when the operating portion is pulled in and pushed out.

10 Claims, 3 Drawing Sheets 4,865,017

ENDOSCOPIC OPERATION INSTRUMENT

BACKGROUND OF THE INVENTION

1. Field of the Invention

This invention relates to an endoscopic operation instrument having an operating portion formed by elastic wires provided with a tendency to expand outwardly.

2. Description of the Prior Art

A basket type forceps, as an endoscopic operation instrument, has an operating portion provided at the distal end of an actuating member slidably inserted in a flexible sheath. This operating portion is formed in such a manner that the proximal ends of elastic wires are connected to the distal end of the actuating member by a rear end tip, that the distal ends of the elastic wires are clamped together by a front end tip, and that bent portions are formed in the intermediate portion of the elastic wires to provide the operating portion with a tendency to expand outwardly. Thus, when the actuating member is pushed and pulled to thrust the operating member out of and into the distal end of the flexible sheath, the operating portion can be opened and closed so as to grasp foreign bodies or remove polyps.

In the operating portion of the above-mentioned conventional endoscopic instrument, the bent portions of the elastic wires are formed at the same position in the axial direction of the actuating member. Therefore, in order to pull the operating portion into the flexible sheath, a plurality of bent portions must be deformed simultaneously, so that the pulling operation is heavy, thereby affecting the handling of the instrument.

Further, when the operating portion has been pulled into the flexible sheath, a plurality of bent portions press against substantially the same position on the inner surface of the flexible sheath, so that the contact resistance therebetween increases. Thus, a large actuating force is also necessary to thrust the operating portion out of the flexible sheath, thereby affecting the handling of the instrument.

The similar problems are observed in the case of a diathermic snare, as another example of endoscopic operation instrument, having an operating portion formed by folding back a single elastic wire.

SUMMARY OF THE INVENTION

An object of the present invention is to provide an endoscopic operation instrument in which an operating portion can be thrust into and out of a flexible sheath by a small actuating force.

An endoscopic operation instrument according to the present invention comprises an operating portion formed by a plurality of elastic wires or a folded-back elastic wire received in the distal end of a flexible sheath, the elastic wires or the folded-back elastic wire being bent in the intermediate portion, wherein the bent portions of the elastic wires are located at different positions. Thus, the handling of the instrument is facilitated when the operating portion is pulled in and pushed out.

DETAILED DESCRIPTION OF THE PREFERRED EMBODIMENTS

Figure 1:
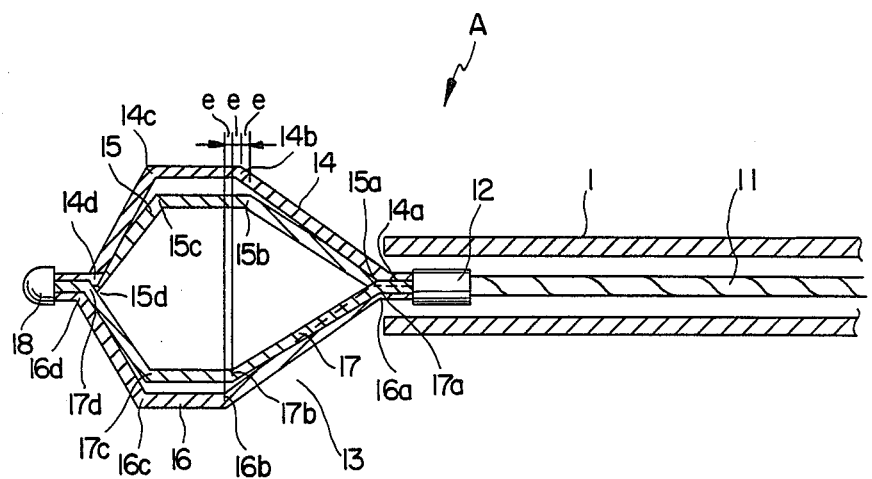
FIG. 1 is a sectional view showing the distal end portion of an endoscopic operation instrument according to an embodiment of the present invention.
Figure 2:
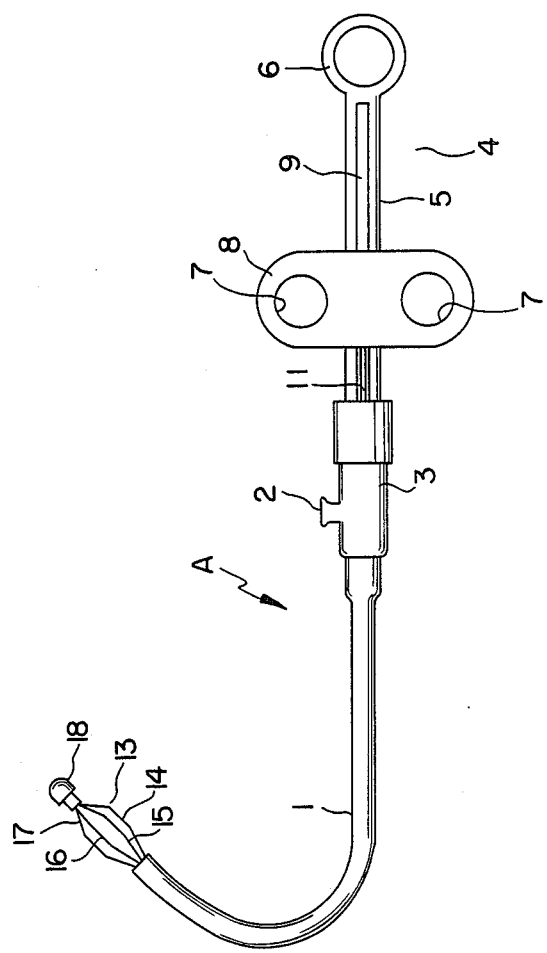
FIG. 2 is a whole view of the endoscopic operation instrument of FIG. 1.

Referring to FIGS. 1 and 2, an embodiment of the present invention is described. FIG. 2 shows a basket type forceps A as an endoscopic operation instrument. The basket type forceps A has a flexible sheath 1. The proximal end of the sheath 1 is connected to a connecting mouthpiece 3 having a liquid feeding opening 2, and an actuating portion 4 is provided at the proximal end of the connecting mouthpiece 3. The actuating portion 4 is formed by a shaft 5, a first finger hole portion 6 formed at the proximal end of the shaft 5, and a slider 8 slidably mounted on the shaft 5 and provided with second finger hole portions 7. A groove 9 is formed in the axial direction of the shaft 5.

As shown in FIG. 1, an actuating wire 11 is slidably inserted in the sheath 1. The actuating wire is connected at its proximal end to the slider 8 and at its distal end to an operating portion 13 by means of a first connecting member 12. The operating portion 13 is formed in such a manner that a plurality of (in this embodiment, four) elastic stranded wires 14, 15, 16 and 17 are connected at their proximal ends to the actuating wire 11 by the first connecting member 12 and clamped together at their distal ends by a second connecting member 18. The first to fourth elastic wires 14 to 17 are provided in consecutive order from their proximal end side with first bent portions 14a to 17a, second bent portions 14b to 17b, third bent portions 14c to 17c, and fourth bent portions 14d to 17d, and these bent portions provide the operating portion 13 with a tendency to expand in the form of a substantially hexagonal basket in its side view. The first bent portions 14a, 15a, 16a and 17a formed in the first to fourth elastic wires 14 to 17 are located at different positions in the axial direction of the sheath 1, and it is just the same with the second, third and fourth bent portions. That is, as shown by intervals e in FIG. 1, the second bent portions 14b, 15b, 16b and 17b are shifted from each other, and other bent portions are also shifted from each other.

In order to pull into the distal end portion of the sheath 1 the operating portion 13 thrust out of the sheath 1 as shown in FIG. 2, the slider 8 is moved backward to draw the actuating wire 11. Then, each elastic wire 14 to 17 urged to expand outwardly comes in contact with the inner surface of the distal end of the sheath 1 and is elastically deformed to be closed and pulled into the distal end portion of the sheath 1. Since the first bent portions 14a to 17a of the first to fourth elastic wires 14 to 17 are shifted from each other in the axial direction of the sheath 1, these portions 14a to 17a are not deformed simultaneously: they are deformed one by one and pulled into the sheath 1. Therefore, compared with the case in which the first bent portions 14a to 17a are deformed simultaneously, pulling resistance is dispersed, so that the actuation can be carried out easily with a small force. Similarly, when the second, third and fourth bent portions 14b to 17b, 14c to 17c, and 14d to 17d are successively pulled into the sheath 1, these bent portions are not deformed simultaneously, thus pulling resistance is dispersed, so that the actuation can be made easily with a small force.

Further, when the operating portion 13 has been pulled into the sheath 1, the bent portions are located at different positions, so that the contact resistance between the bent portions and the inner surface of the sheath 1 is dispersed. Therefore, the operating portion 13 pulled into the sheath 1 can be thrust out as easily as it is pulled in.

Figure 3:
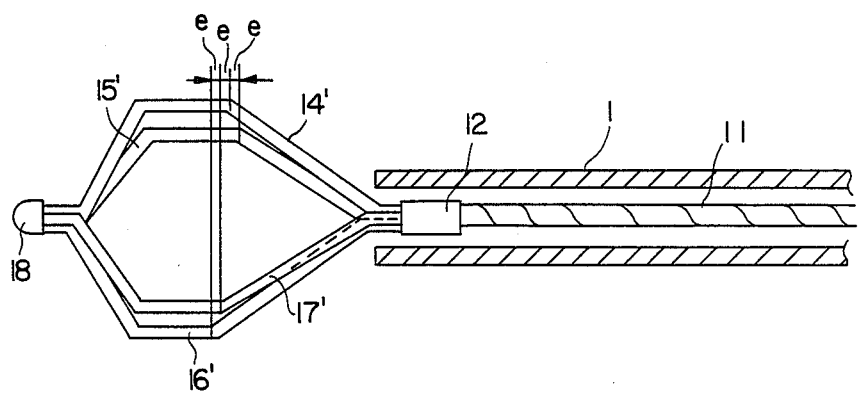
FIG. 3 is a sectional view showing the distal end portion of an endoscopic operation instrument according to another embodiment of the present invention.

FIG. 3 shows another embodiment of the present invention. This embodiment differs from that shown in FIG. 1 only in the type of elastic wires. That is, the embodiment of FIG. 1 uses stranded elastic wires 14, 15, 16 and 17 while this embodiment employs single elastic wires 14', 15', 16' and 17'. Since other elements are the same as those of the embodiment of FIG. 1, their description is omitted.

Figure 4:
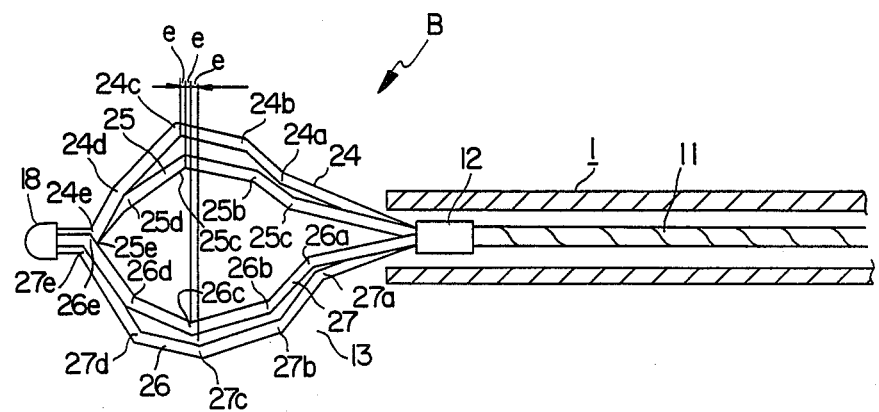
FIG. 4 is a sectional view showing the distal end portion of an endoscopic operation instrument according to still another embodiment of the present invention.

FIG. 4 shows still another embodiment of the present invention. This embodiment differs from that shown in FIG. 3 only in the form of the operating portion 13, and other elements are the same as those of the embodiment of FIG. 3. An operating portion 13 of a basket type forceps B is formed in such a manner that a plurality of (in this embodiment, four) single elastic wires 24, 25, 26 and 27 are connected at their proximal ends to an actuating wire 11 by a first connecting member 12 and clamped together at their distal ends by a second connecting member 18. The first to fourth elastic wires 24 to 27 are provided in consecutive order from their proximal end side with first bent portions 24a to 27a, second bent portions 24b to 27b, third bent portions 24c to 27c, fourth bent portions 24d to 27d, and fifth bent portions 24e to 27e, and these bent portions provide the operating portion 13 with a tendency to expand in the form of a substantially octagonal basket in its side view. Similar to the embodiments of FIGS. 1 and 3, the first bent portions 14a, 15a, 16a and 17a are located at different positions in the axial direction of a sheath 1, and it is just the same with second, third, fourth and fifth bent portions. That is, as shown by intervals e in FIG. 4, the third bent portions 24c, 25c, 26c and 27c are shifted from each other, and other bent portions are also shifted from each other. Therefore, similar to the embodiments of FIGS. 1 and 3, when the operating portion 13 is thrust into and out of the sheath 1, respective bent portions are not deformed simultaneously in the same form, thereby enabling easy pulling and pushing of the operating portion 13 with a small force.

Although single wires are used as the elastic wires 24 to 27 in this embodiment, stranded wires also may be employed.

Figure 5:
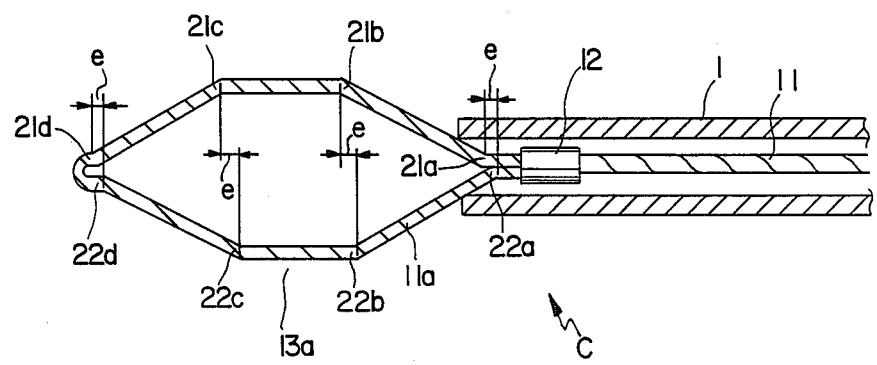
FIG. 5 is a sectional view showing the distal end portion of an endoscopic operation instrument according to still another embodiment of the present invention.

FIG. 5 shows still another embodiment of the present invention. An operating portion 13a of a diathermic snare C as an endoscopic operation instrument is formed by folding back a stranded elastic wire 11a. Similar to the embodiments of FIGS. 1, 3 and 4, both halves of the elastic wire 11a are provided with first bent portions 21a and 22a, second bent portions 21b and 22b, third bent portions 21c and 22c, and fourth bent portions 21d and 22d. One of the first bent portions 21a and 22a are shifted from the other by an interval e, and it is just the same with other bent portions. Thus, also in this case, the operating portion 13a can be thrust in and out easily with a small force. Naturally, the stranded elastic wire used in this embodiment may be replaced with a single elastic wire.

As many apparently widely different embodiments of this invention may be made without departing from the spirit and scope thereof, it is to be understood that the invention is not limited to the specific embodiments thereof except as defined in the appended claims.

What is claimed is:

1. An endoscopic operation instrument comprising an operating portion formed by a plurality of elastic wires received in the distal end of a flexible sheath, the elastic wires being bent in the intermediate portion, wherein the bent portions of the elastic wires are located at different positions in the axial direction of the sheath.

2. An endoscopic operation instrument according to claim 1, wherein the endoscopic operation instrument is a basket type forceps having a basket-shaped operating portion.

3. An endoscopic operation instrument according to claim 2, wherein the respective elastic wires forming the basket-shaped operating portion are substantially hexagonal in their side view.

4. An endoscopic operation instrument according to claim 2, wherein the respective elastic wires forming the basket-shaped operating portion are substantially octagonal in their side view.

5. An endoscopic operation instrument according to claim 1, 2, 3 or 4, wherein the elastic wires are stranded wires.

6. An endoscopic operation instrument according to claim 1, 2, or 4, wherein the elastic wires are single wires.

7. An endoscopic operation instrument comprising an operating portion formed by a folded-back elastic wire received in the distal end of a flexible sheath, the elastic wire being bent in the intermediate portion, wherein the bent portions of the elastic wire are located at different positions in the axial direction of the sheath.

8. An endoscopic instrument according to claim 8, wherein the endoscopic operation instrument is a diathermic snare.

9. An endoscopic instrument according to claim 7 or 8, wherein the folded-back elastic wire is a stranded wire.

10. An endoscopic instrument according to claim 7 or 8, wherein the folded-back elastic wire is a single wire.

* * * * *